United States Patent
Walker

(12) 
(10) Patent No.: US 6,565,860 B1
(45) Date of Patent: May 20, 2003

(54) SURFACTANT COATED PRODUCTS AND METHODS FOR THEIR USE IN PROMOTING PLANT GROWTH AND SOIL REMEDIATION

(75) Inventor: Richard T. Walker, Senatobia, MS (US)

(73) Assignee: Jay-Mar, Inc., Plover, WI (US)

( * ) Notice: Subject to any disclaimer, the term of this patent is extended or adjusted under 35 U.S.C. 154(b) by 0 days.

(21) Appl. No.: 09/567,336

(22) Filed: May 9, 2000

Related U.S. Application Data

(60) Provisional application No. 60/134,266, filed on May 14, 1999.

(51) Int. Cl.[7] .................................................. A61K 9/16
(52) U.S. Cl. ........................ 424/400; 424/489; 424/493; 71/31; 71/48; 71/58; 71/64.07; 71/64.11; 71/64.13
(58) Field of Search ................................. 504/100, 102, 504/116.1, 118; 424/405, 408, 409, 417, 418, 421, 400, 489, 493; 71/64.02–64.07, 64.11, 64.13, 31–36, 48–54, 58–63

(56) References Cited

U.S. PATENT DOCUMENTS

| | | | |
|---|---|---|---|
| 5,026,734 A | 6/1991 | Browning | 514/723 |
| 5,141,963 A | 8/1992 | Browning | 514/723 |
| 5,143,939 A | 9/1992 | Browning | 514/723 |
| 5,391,542 A | 2/1995 | Browning | 504/351 |
| 5,429,654 A | 7/1995 | Swarup | 71/64.07 |
| 5,484,600 A | 1/1996 | Sjogren | 424/405 |
| 5,516,520 A | 5/1996 | Yang et al. | 424/408 |
| 5,516,747 A | 5/1996 | Lachut | 504/116 |
| 5,532,305 A | 7/1996 | Matsuzaki et al. | 525/54.2 |
| 5,563,112 A * | 10/1996 | Barnes III | 504/125 |
| 5,565,407 A | 10/1996 | Southard | 504/116 |
| 5,576,008 A | 11/1996 | Yang et al. | 424/408 |
| 5,652,196 A | 7/1997 | Luthra et al. | 504/116 |
| 5,663,117 A * | 9/1997 | Warner | 504/206 |
| 5,750,130 A | 5/1998 | Ferrell et al. | 424/417 |
| 5,859,218 A | 1/1999 | Wulff et al. | 536/18.6 |
| 5,928,993 A * | 7/1999 | Johansson | 504/116 |
| 6,184,182 B1 * | 2/2001 | Gillespie et al. | 504/116 |

FOREIGN PATENT DOCUMENTS

| | | | |
|---|---|---|---|
| GB | 2174689 | * | 11/1986 |
| JP | 63-250305 | * | 10/1988 |

OTHER PUBLICATIONS van Zundert, Marga, "Alkyl polyglycosides, renewable surfactants from coconut and corn", *Carbohydrates in Europe* 18:18–26 (1997).

* cited by examiner

*Primary Examiner*—Neil S. Levy
(74) *Attorney, Agent, or Firm*—Howrey Simon Arnold & White, LLP

(57) ABSTRACT

Novel mixed agricultural compositions, and methods for their use are disclosed. The agricultural compositions are prepared by a process comprising mixing together a carrier, such as a solid fertilizer or liquid solvent, and a carbohydrate-based surfactant, such as AGRIMUL PG 2069 (Henkel, Dusseldorf, Germany). For example, 8 quarts of surfactant were mixed with one ton of a solid fertilizer. The carrier material can further comprise biologically active agents such as herbicides, insecticides, chemosterilants, nematicides, and fungicides. These mixed agricultural compositions are used to promote the growth of plants in soil and enhance soil bioremediation.

7 Claims, No Drawings

SURFACTANT COATED PRODUCTS AND METHODS FOR THEIR USE IN PROMOTING PLANT GROWTH AND SOIL REMEDIATION

The application claims priority from U.S. Provisional Application Ser. No. 60/134,266, filed May 14, 1997, the entire contents of which are incorporated by reference herein.

FIELD OF THE INVENTION

The present invention relates to mixed agricultural compositions and methods for their use. Specifically, a carrier material comprising a fertilizer, pesticide or anti-caking agent is mixed with a carbohydrate-based surfactant. The mixed agricultural compositions may be used to improve plant growth, enhance pest control, or facilitate soil bioremediation.

BACKGROUND OF THE INVENTION

It is known that soil with a healthy microorganism population is best suited for effective pest control, robust plant growth, and efficient biodegradation of unwanted soil contaminants. Soil microorganisms break down dead plant and animal material and mediate the biodegradation of most man-made pesticides. To thrive, these microorganisms require a readily available source of carbon for food. Furthermore, it is more desirable to stimulate the proliferation of indigenous soil microorganisms than to add microorganisms from an external source.

It is known that gradual release of fertilizer nutrients and biologically active agents such as pesticides into the soil is advantageous as it avoids potential toxicity resulting from sudden increases in soil concentrations of applied substances.

Many controlled release methods for fertilizers and pesticides have previously been disclosed. For example, in U.S. Pat. No. 5,484,600, Sjogren discloses a method for making a composite particle capable of releasing insecticides at a slow or controlled rate. In U.S. Pat. No. 5,576,008, Yang et al. disclose a method for the microencapsulization of insecticides into a urea-formaldehyde resin. In U.S. Pat. No. 5,516,520, Yang et al. disclose a method of preparation and use of a pesticide encapsulated in a starch-borax-urea matrix for controlled release. In U.S. Pat. No. 5,565,407, Southard discloses improved bioactive agent release-extending compositions of native, undenatured starch and biodegradable synthetic polymers. In U.S. Pat. No. 5,652,196, Luthra et al. disclose products for the variable controlled release of water soluble plant nutrients consisting of a core of water soluble agent coated with an organic film-forming thermoplastic or thermosetting compound and a thermoplastic resin to control release. In U.S. Pat. No. 5,429,654, Swarup discloses a method of improved fertilizer release control comprising coating a fertilizer with a neutralized, sulfonated EPDM polymer having a measurable degree of crystallinity. In U.S. Pat. No. 5,750,130, Ferrell et al. disclose a method of applying a pesticide to inert organic or inorganic granular substrates using a carrier compound to improve adhesion of the pesticide to the substrate and to improve control over the release of the pesticide.

It is desirable to avoid the use of foreign materials, or materials which are not otherwise useful for growing plants, when developing methods for the more effective utilization of fertilizers and pesticides, as this allows for enhanced growth and protection of plants without the introduction of complex and expensive matrix components.

In U.S. Pat. Nos. 5,391,542 and 5,143,939, Browning discloses the use of surfactants such as the TERGITOL series of surfactants (TERGITOL is a registered trademark of Union Carbide Corporation, Danbury, Conn.) as a liquid soil additive to enhance the germination and subsequent growth of plants. Browning also describes the use of the liquid soil additive as a method of nematode, worm, mite, and fungus control. However, the surfactant is only effective for a limited period of time following application to the soil.

There exists a need in the art for an improved soil treatment which expedites proliferation of the native soil microorganisms more efficaciously than the non-mixed products alone. Such a treatment should ideally enhance pest control, plant growth, and the bioremediation of pesticide residues in the soil.

SUMMARY OF THE INVENTION

The present invention is directed to an agricultural composition prepared by a process comprising mixing together a carbohydrate-based surfactant with a soil additive carrier. The carrier material may be any liquid or solid core material which is compatible with the present invention. The solid core material typically comprises a solid soil additive, such as an organic fertilizer, inorganic fertilizer, pesticide, or anti-caking agent, that is preferably provided as a powder, granule, pellet, or any other compatible solid form. The carrier material may generally be any formulation having agricultural utility.

As used herein the term "mixing" includes the activities of mixing, contacting, blending, stirring, coating, applying, impregnating, commingling, amalgamating, or coalescing.

The solid core material may further comprise a biologically active agent. The biologically active agent is typically selected to bestow additional functional properties to the mixed agricultural composition. Exemplary biological agents include herbicides, insecticides, chemosterilants, nematicides, and fungicides.

The solid core material is typically mixed with a carbohydrate-based surfactant, preferably an alkyl polyglycoside; categories of alkyl polyglycoside include: alkyl glucosides, fatty acid glucamides, sucrose fatty acid esters, and sorbitan fatty acid esters. Typically, the amount of surfactant is less than about 1% (w/w) of the final composition. The surfactant is generally used at a concentration of about 400 grams to about 7700 grams per U.S. ton of solid core material. The mixed agricultural composition is preferably applied at a rate between about 125 pounds and about 1000 pounds per acre.

The agricultural compositions of this invention are useful for promoting the growth of plants and enhancing bioremediation of contaminated soil. These mixed agricultural compositions, when applied to the soil, can increase soil microorganism populations relative to non-mixed fertilizers, pesticides, or surfactants alone. They can also exhibit fewer of the toxic effects normally associated with the application of pesticides and surfactants delivered as unmixed formulations.

DETAILED DESCRIPTION OF THE INVENTION

The present invention relates to a mixed agricultural composition prepared by a process comprising mixing together a soil additive carrier material and a carbohydrate-based surfactant, methods for producing the composition, and uses thereof. The carrier material may generally be a liquid or a solid core material. In particular, the solid core material is mixed, impregnated, or coated with a carbohydrate-based surfactant. The solid core material may comprise an organic fertilizer, inorganic fertilizer, anti-caking agent, herbicide, insecticide, chemosterilant, nematicide, fungicide or combinations of such materials.

As used herein, the term "soil additive" refers to fertilizers, anti-caking agents, pesticides, ditomaceous earth, calcium sulfate, corn cob particulate, bentonite clay, vermiculite and combinations thereof.

The solid core material generally comprises a powdered, particulate, granular, pelleted, or any other compatible solid form of soil additive, such as, for example, an organic or inorganic fertilizer. The organic fertilizer may be any compatible organic fertilizer and is preferably HOU-ACTINITE (Houston, Tex.), or MILORGANITE (Milwaukee, Wis.). The inorganic fertilizer may generally be any fertilizer having agricultural utility including ammonium nitrate, ammonium sulfate, ammonium polyphosphate, calcium sulfate, calcium nitrate, calcium sulfate, diammonium phosphate, triple super phosphate, single super phosphate, lime or limestone, magnesium sulfate, manganese sulfate, monoammonium phosphate, monocalcium phosphate, potassium nitrate, potassium chloride, potassium magnesium sulfate, sulfate of potash, sodium nitrate, sulfur-coated urea, borax, pelleted fertilizers, fertilizers coated for slow release, or mixtures thereof.

The solid core material may also include various inert substances which may not directly contribute to the overall nutrient value of the agricultural composition. Such substances may include solid carriers, drying agents, or anti-caking agents such as diatomaceous earth, calcium sulfate, corn cob particulate, bentonite clay, vermiculite, or combinations of these substances.

The solid core material may further comprise a biologically active agent. The biologically active agent is typically selected to bestow additional functional properties to the mixed agricultural composition. Exemplary biological agents include herbicides, insecticides, chemosterilants, nematicides, and fungicides.

The herbicide may generally be any herbicidal agent compatible with the present invention. The herbicide preferably is an amide, aromatic acid, arsenical, benzoylcyclohexanedione, benzofuranyl alkylsulfonate, carbamate, carbanilate, cyclohexene oxime, cyclopropylisoxazole, dinitroaniline, dinitrophenol, diphenyl ether, halogenated aliphatic, imidazolinone, inorganic, nitrile, organophosphorus, phenoxy, phenylenediamine, pyrazolyloxyacetophenone, pyrazolylphenyl, pyridazinone, pyridine, pyrimidine diamine, quaternary ammonium, thiocarbamate, thiocarbonate, triazine, triazole, triazolopyrimidine, uracil, urea, unclassified herbicide, or a mixture thereof, more preferably is a dinitroaniline herbicide, and most preferably is trifluralin.

The insecticide may generally be any insecticidal agent compatible with the present invention. The insecticide preferably is antibiotic, arsenical, botanical, carbamate, dinitrophenol, fluorine, formamidine, fumigant, hydrazide, growth regulatory, nereistoxin analogue, nitromethylene, organochlorine, organophosphorus, oxadiazine, pyrazole, pyrethroid, pyridine, unclassified insecticide, or a mixture thereof.

The chemosterilant may generally be any chemosterilant agent compatible with the present invention. The chemosterilant is preferably apholate, bisazir, busulfan, diflubenzuron, dimatif, hemel, hempa, metepa, methiotepa, methyl apholate, morzid, penfluron, tepa, thiohempa, thiotepa, tretamine, or a mixture thereof.

The nematicide may generally be any nematicidal agent compatible with the present invention. The nematicide is preferably an antibiotic, carbamate, organophosphorus, unclassified nematicide, or a mixture thereof.

The fungicide may generally be any fungicidal agent compatible with the present invention. The fungicide is preferably an aliphatic, anilide, antibiotic, aromatic, benzimidazole, benzimidazole precursor, carbamate, conazole, copper, dicarboximide, dinitrophenol, dithiocarbamate, imidazole, mercury, morpholine, organophosphorus, organotin, oxazole, phenylsulfamide, phenylurea, pyridine, pyrimidine, quinoline, quinone, quinoxaline, thiazole, thiocarbamate, triazole, xylylalanine, unclassified fungicide, or a mixture thereof.

The solid core material is typically mixed with a carbohydrate-based surfactant. The carbohydrate-based surfactant preferably comprise an alkyl polyglycoside. The alkyl polyglycosides comprise compounds represented by the general formula:

$$R\text{---}O(G)_n$$

wherein (R) is a straight or branched chain, saturated or unsaturated, oxo-substituted or unsubstituted $C_{8-22}$ alkyl or aliphatic radical; (G) is a glycose residue; and (n) is an integer of from about 1 to about 10.

The above alkyl polyglycosides present in surfactant mixtures and their production are described, for example, in European patent applications EP 92 355, EP 301 298, EP 357 969, EP 362 671 and U.S. Pat. No. 3,547,828.

The alkyl or aliphatic radical represented by (R) in the formula above is preferably $C_{8-18}$, and more preferably $C_{9-19}$, and even more preferably $C_{9-14}$. The degree of polymerization or oligomerization, DP, represented by (n) in the formula above is preferably any integer from about 1 to about 10; more preferably (n) is between about 1 and about 2. The glycose residues represented by (G) in the formula above preferably comprise any naturally occurring or synthetic aldose or ketose monomer, including but not limited to glucose, mannose, ribulose xylulose, psicose, sorbose, tagatose, fructose, galactose, talose, gulose, altrose, allose, idose, ribose, arabinose, xylose and lyxose or any combination thereof. Since the reaction products of sugars and alcohols are generally mixtures, the term "alkyl polyglycoside" encompasses both alkyl monoglycosides and alkyl poly (oligo) glycosides. By virtue of its ready availability, glucose is the preferred glycose monomer residue.

These alkyl polyglycoside surfactants are characterized not only by the type of glycose residues present, but also by their number, the so called degree of polymerization, or DP. One consequence of this is that alkyl polyglycoside-based surfactants may include 100% of a particular alkyl polyglycoside species or it may be include of a mixture comprising any combination of the described alkyl polyglycosides. Therefore, as an analytically determined quantity, the DP for any given surfactant composition is expressed as the ratio of the number of glycoside residues, (G) in the formula above, to aliphatic groups, (R) in the formula above, for all of the various alkyl polyglycosides present in the composition. This ratio is preferably between about I and about 10; more preferably the ratio is between about 1.0 and about 2.0; and most preferably it is between about 1.1 and about 1.8.

The straight or branched chain alkyl or aliphatic radical, represented by (R) in the formula above, is preferably obtained from any available derivatives of renewable raw materials or from synthetic sources; possible sources include, but are not limited to fatty alcohols, branched-chain primary alcohols, or the so-called oxo-alcohols. Oxo-alcohols, also known as Ziegler alcohols, typically comprise an odd number of carbon atoms preferably between about 7 carbon atoms and about 19 carbon atoms.

Using standard production methods, the alkyl polyglycosides may include small quantities (typically less than about 5%) of other compounds such as salts, unreacted long-chain alcohols, or other impurities which are compatible with the present invention.

The surfactant is more preferably an alkyl polyglycoside represented by the formula:

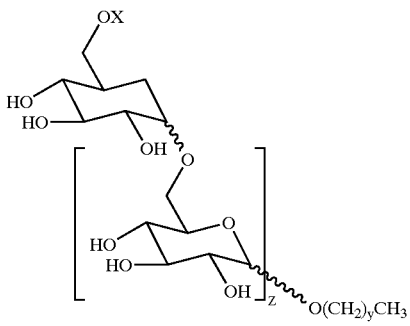

Wherein (y) is an integer from 7 to 21; (z) is any number of about 10 or less and represents the average degree of glycoside polymerization which is based on the ratio of glycoside residues to alkyl or aliphatic groups for all of the various alkyl polyglycoside molecules present in the surfactant; and (x), is defined as a carbonate group, ethercarboxylate group, ether group, ethoxylate group, ester group, hydrogen atom, isethionate group, quaternary group (e.g. a quaternary amine), sulfate group, or sulfosuccinate group; more preferably (y) is from about 9 to about 14, (z) is between about 1.0 and about 2.0, and more preferably between about 1.1 and about 1.8, and x is preferably an hydrogen atom.

Due to the nature of glycosidic bond formation the surfactant may include a complex mixture of glycoside products comprising alpha- and/or beta-anomers in pyranose and/or furanose ring structures. Furthermore, these residues may be joined by any combination of (1-6)-, (1-4)-, (1-2)-, and (1-3)- glycosidic linkages.

Exemplary surfactants include the AGRIMUL PG series, preferably AGRIMUL PG 2069 (Henkel AG, Dusseldorf, Germany).

The surfactant is preferably mixed with the solid core material at a concentration between about 400 grams and about 7700 grams per U.S. ton of solid core material, and more preferably between about 400 grams and about 2900 grams per U.S. ton of solid core material. These mixed agricultural compositions are preferably applied at a rate between about 125 pounds and about 1000 pounds per acre.

The surfactant is typically provided in a liquid form. For instance, a liquid surfactant containing about 50% (v/v) alkyl polyglycoside is commercially available as AGRIMUL PG 2069 (Henkel, Dusseldorf, Germany). This solution can be used directly or diluted with a suitable carrier prior to use. When mixed with a solid core material the liquid surfactant, or diluted liquid surfactant, is preferably sprayed onto the solid core material.

The mixture of surfactant and solid core material may become wet and difficult to manage when the quantity of surfactant added reaches the upper range of the application amount. If the mixture becomes wet, drying agent components such as bentonite clay or calcium sulfate, may be added in an amount sufficient to reduce the moisture level of the composition. The amount of drying agent added is typically between about 5 pounds and about 50 pounds per U.S. ton of solid core material.

Dry fertilizers are often blended using large mixing devices or payloaders in which the fertilizer and various additives have been added. Transfer of scoopfulls of components into the mixture with a spreading action eventually produces a homogeneous mixture. During the process of mixing, an appropriate quantity of surfactant (as described above) may be sprayed onto the mixture to produce a uniform coating of the surfactant on the fertilizer blend. In addition, an appropriate concentration of a biologically active agent, such as a pesticide or herbicide, may be added to the mixed fertilizer blend. The biologically active agent is mixed with the fertilizer so that the agent is evenly distributed in the final product. The use of a surfactant greatly aids the process of impregnating fertilizer granules with biologically active agents, presumably due to the enhanced penetrating qualities often observed with surfactants. The mixed agricultural composition is preferably used in the field at a rate between about 125 and about 1000 pounds per acre.

The invention is further directed to methods of using the above mixed agricultural compositions to promote plant growth in soil and enhance control of various agricultural pests. The method of promoting the growth of plants in soil generally comprises the steps of obtaining an agricultural composition mixed with a carbohydrate-based surfactant (as described above), and applying the composition to the soil.

The applicants have found that the use of agricultural compositions comprising carbohydrate-based surfactants produces remarkably increased plant growth and provides significantly enhanced bioremediation activity relative to other agricultural compositions currently available.

Use of the carbohydrate-based surfactant/fertilizer compositions may allow the plants to more effectively utilize the fertilizer nutrients by reducing surface tension at the plant-water interface. This enhances the ability of the nutrient solution to cover and penetrate plant surfaces. The surfactant and nutrients are released into the soil from the fertilizer granules in a gradual and sustained manner by natural erosion processes. The mixed compositions will supply a readily accessible source of carbon that stimulates the rapid growth of beneficial soil microorganisms. These microorganisms will break down organic matter and minerals into form more easily used by plants.

By incorporating biological agents into a mixed agricultural composition, the release of these biological agents is controlled and maintained over an extended period of time. This prolonged release is generally superior to immediate release because it increases the time over which the treatment is effective and reduces the deleterious effects on plants caused by the high concentrations of these agents which results from unregulated release immediately upon application. For example, biologically active agents such as pesticides are often toxic to plants during the sudden concentration "spike" which immediately follows application. The mixed agricultural compositions maintain a continual steady rate of release, thus avoiding toxic "spikes" in concentration.

Additionally, leaching of these biologically active agents into groundwater is reduced due to the controlled release properties exhibited by the mixed agricultural composition. At any given time, only a fraction of the total applied quantity of biologically active agent will be free in the soil to be washed off the field by rainfall or irrigation.

Consequently, fewer applications of the agricultural composition are required as the applied agent remains on the field longer. Since an increased percentage of the agricultural composition will remain in the soil for a longer period of time, the total quantity of biologically active agent needed for the initial application is reduced. This decreases the total cost and is environmentally beneficial.

The method of the present invention avoids the use of foreign materials or materials which are not otherwise useful for growing plants. It utilizes the natural slow release properties of typical granular fertilizer formulations as a vehicle for the controlled and continuous release of surfactants (with or without additional biologically active components) to soil to enhance fertilizer nutrient uptake and efficiency of biologically active agents. This allows for enhanced growth of plants without requiring the introduction of complex and expensive matrix components. Other controlled release fertilizer formulations do not describe the benefit of incorporating surface active agents into the matrix or formulation to improve plant nutrient utilization efficiency.

Additional methods of the present invention are directed toward the use of granular or solid fertilizers as a gradually eroding matrix from which impregnated surfactants and bioactive products are released to mediate their own growth promoting, bioremediative, herbicidal, insecticidal, chemosterilant, nematicidal, or fungicidal effects over time. These further methods also allow for a longer and more controlled release of the surfactant from the mixed agricultural composition. Since the described method more effectively regulates the release of surfactant, the total amount of surfactant required is minimized and the cost is reduced. Also, the use of complex and expensive matrix components containing foreign materials, or materials which are not intrinsically useful for growing plants, is avoided.

The present invention is further directed to methods of using agricultural compositions comprising carbohydrate-based surfactants to facilitate the bioremediation of contaminated soil. Bioremediation involves the use of living organisms to break down organic and inorganic contaminants into more basic components, thereby eliminating environmental pollutants, restoring contaminated sites, and preventing the accumulation of further pollutants. Generally, bioremediation is accomplished using bacteria, although other microorganisms, namely fungi and algae, have been used. See, for example, Ronald M. Atlas, *Chemical & Engineering News,* Apr. 3, 1995, pp. 32–42. The present invention is believed to function in part by serving as a nutrient source for the microorganisms responsible for bioremediation.

There are a variety of chemicals which may be refractory to spontaneous chemical breakdown and thus persist in the environment. Such contaminants may or may not be inherently toxic to the environment; for instance, nitrates are not inherently toxic (minimum quantities are essential in order for most plants to thrive), however, excessive quantities of nitrates may have deleterious ecological effects.

Potential targets for bioremediation for use with the present invention may include any common inorganic or organic contaminant found in the environment and more preferably includes pesticides, insecticides, growth regulators, growth inhibitors, toxicants, bactericides, attractants, repellents, hormones, molluscicides, defoliants, chemosterilants, fumigants, systemics, rodenticides, avicides, detergents, surfactants, nematicides, acaricides, miticides, predicides, herbicides, agricultural chemicals, algicides, fungicides, sterilants; polycyclic aromatic hydrocarbons (PAH's), polychlorinated biphenyls (PCB's), greasy wastes, solvents, crude oil, diesel fuel, waste oil, Bunker "C" oil, phenolics, halogenated hydrocarbons, citrus juice processing wastes, terpene alcohols, starchy carbohydrates, and the like.

Specific organic contaminants may include anthracene, chlorotoluenes, chrysene, cresols, di-N-octylphthalate, dichlorobenzene, dichlorethanes, dichloropropanes, dichlorotoluene, 2-ethoxyethanol, ethylene glycol, ethylene glycol monoethyl ether acetate, ethylbenzene, fluorene, isoprenoids, methyl ethyl ketone, methylene chloride, naphthalene, pentachlorophenol, phenanthrene, 1,1,2,2-tetrachloroethane, toluene, 1,1,2-trichloroethane, trichloroethylene, benzoate, chlorobenzoates, methanol, ethyl acetate, cyclohexanone, ethylbenzene, 2,4-dichlorophenoxyacetic acid, 2,4,5-trichlorophenoxy-acetic acid, m,o,p-xylene, butyl acetate, camphor, hexane, heptane, octane, nonane, d-limonene, linalool, geraniol, citronellol.

Herbicides are a particularly common agricultural contaminant. Classes of herbicidal contaminants found in the soil may include: amides, aromatic acids, arsenicals, benzoylcyclohexanediones, benzofuranyl alkylsulfonates, carbamates, carbanilates, cyclohexene oximes, cyclopropylisoxazoles, dinitroanilines (such as trifluralin), dinitrophenols, diphenyl ethers, halogenated aliphatics, imidazolinones, inorganic herbicides, nitriles, organophosphorus herbicides, phenoxy herbicides, phenylenediamines, pyrazolyloxyacetophenones, pyrazolylphenyls, pyridazines, pyridazinones, pyridines, pyrimidinediamines, quaternary ammonium herbicides, thiocarbamates, thiocarbonates, triazines (such as atrazine), triazinones, triazoles, triazolopyrimidines, uracil herbicides, urea herbicides, unclassified herbicides, or a mixture thereof.

The composition described herein may act as a nutrient source for microbial agents, thereby stimulating their growth. Alternatively, the application of the composition to the soil may result in an exothermic reaction which attracts the microbes, thereby bringing them to a nutrient rich environment. The term "microbial agent" is meant to include microorganisms that enhance biodegradation processes. These microorganisms include bacteria, fungi, and algae, or combinations of these microorganisms, for example. Furthermore, as used herein, "biodegradation" means the chemical alteration and breakdown of a substance caused by microorganisms and their enzymes. Contaminants that are biodegradable include any compound that can be microbially mineralized into carbon dioxide, water, ammonia and/or chloride, or that can be transformed into a non-hazardous intermediate.

As a method for enhanced bioremediation, carbohydrate-based surfactants may be applied to a contaminated area in a generally pure state; diluted in a suitable liquid solvent, aqueous or otherwise; or mixed with a suitable solid core matrix. In addition, the composition may be further mixed with any biological agent which is compatible with the present invention. Exemplary biological agents include pesticides, herbicides, insecticides, growth regulators, toxicants, bactericides, molluscicides, chemosterilants, rodenticides, avicides, nematicides, acaricides, algicides, fungicides, predicides, or any variant or combination thereof.

As a method for enhanced bioremediation, the amount of carbohydrate-based surfactant applied to soil is preferably between about 0.25 quarts per acre and about 4.0 quarts per acre and more preferably between about 0.5 quarts per acre and about 1.25 quarts per acre.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Mixing the Fertilizer Blend

Often dry fertilizers are blended with small amounts of additives through the use of large mixing devices. In some cases, a payloader is used in which the components are blended through the process of picking large scoopfulls of a fertilizer component and spreading it over another component. Transfer of scoopfulls of components into the mixture with a spreading action eventually achieves an evenly distributed mixture. Other methods for blending dry fertilizer are well known in the art. For example, a large drum shaped container capable of holding the desired volume of dry ingredients and able to rotate at an inclined angle along the center axis may be used. Dry components are added to the drum during rotation to facilitate a mixing or blending action. Often the drum has a method for spraying liquid mixtures onto the dry fertilizer components. This serves to impregnate or coat the surface of the fertilizer blend with these liquid materials. Frequently, these methods of incorporating a liquid material into a fertilizer matrix involve the use of a liquid pump and nozzles to propel small droplets onto the dry fertilizer components so that the liquid is evenly distributed.

During the process of mixing, a small amount of fluid such as a surfactant, such as AGRIMUL PG 2069 (Henkel, Dusseldorf, Germany) can be sprayed onto the mixture to achieve a uniform coating on the particles. At this time a pesticide may be incorporated into the mixture following rate guidelines specified by the pesticide label.

By using different amounts of a given fertilizer component, a desired level and ratio of nitrogen, phosphorous and potassium also known as the NPK values, may be achieved. For example to produce a U.S. ton of a mixture containing an NPK level of 16-16-18 one would mix 700 pounds of urea to 700 pounds of super triple phosphate to 600 pounds of course potash. This fertilizer blend has an NPK composition of 22-4-12+7S.

Example 2

Production of an Agricultural Composition Comprising Fertilizer Mixed with AGRIMUL PG 2069

In a large blending device the following materials were added during the mixing process: 384 pounds of Course Potash; 174 pounds of Diammonium Phosphate (DAP); 584 pounds of Ammonium Sulfate; 858 pounds of Ammonium Nitrate. These materials were mixed until an even distribution was achieved. During the later stages of this blending process, the liquid surfactant AGRIMUL PG 2069 was sprayed onto the dry mixture of fertilizer. The liquid was sprayed by the use of a pump to pressurize the liquid and nozzles to control and direct the spray. In this example, 8 quarts of the liquid AGRIMUL PG 2069 were sprayed onto the blended fertilizer. As the AGRIMUL 2069 reaches a high level, the mixture becomes somewhat wet and difficult to manage. As this occurs, drying agents such as bentonite clay or calcium sulfate may be used at a rate of between 5–50 pounds per U.S. ton of fertilizer mixture.

Example 3

Testing the Plant Growth Promoting Properties of an Agricultural Composition Comprising Fertilizer Mixed with AGRIMUL PG 2069

The composition of Example 2 was tested for its ability to promote plant growth. The test was conducted in Avon Park, Fla. starting in the fall and continuing through January and February. It was tested on 100 ft$^2$ plots of Lake Wales ridge sand soil type in an area which was previously not productive due to stresses caused by a low soil microbe count and a high nematode load. The test was conducted using the hybrid bermudagrass turf type. The agricultural composition was applied at a rate of 250 pounds per acre (1 quart/acre). Five random locations for each plot were tested by taking a core sample using a golf-green hole cutter. This was done prior to treatment and then at 14, 30, and 60 days post-treatment. Each sample was carefully washed so as not to damage or remove roots. The samples were assessed for root mass and length. Experimental control treatments included untreated soil and soil treated with the nematicide SAFE-T-GREEN at an application rate of 1 quart per acre. The results of this experiment are summarized in Table 1.

TABLE 1

Promotion of Plant Growth by an Agricultural composition which includes AGRIMUL PG 2069

| Treatment (as described in text) | Pre-treatment Turf Root length (inches) | 14 Days Post-treatment Turf Root length (inches) | 30 Days Post-treatment Turf Root length (inches) | 60 Days Post-treatment Turf Root length (inches) |
| --- | --- | --- | --- | --- |
| Control (No treatment) | 2.0 | 2.0 | 2.0 | 2.0 |
| SAFE-T GREEN | 2.0 | 2.8 | 2.6 | 2.4 |
| AGRIMUL PG 2069 | 2.0 | 2.8 | 4.4 | 6.0 |

The data summarized by this table clearly indicates that AGRIMUL PG 2069 mixed with fertilizer is a superior growth promoting agricultural composition. In soils previously unable to promote root growth due to a high nematode load and low microbial population the AGRIMUL PG 2069 composition out-performed the nematicide SAFE-T GREEN and the control in stimulating turf root growth. In addition to dramatically increasing root length, the AGRIMUL PG 2069 composition substantially improved root quality by stimulating the growth of new secondary root branches, or hairs, thereby maximizing root surface area and nutrient absorption.

Example 4

Testing the Toxicity to Soil Microbes of an Agricultural Composition Comprising Fertilizer Mixed with AGRIMUL PG 2069

The composition of Example 2 was tested for its effect on soil microbial activity. Soil was treated as described in Example 3. Soil samples were taken with a soil probe at five random plot locations both prior to treatment and again at 60 days post-treatment. The samples were analyzed by A&L Laboratories (Memphis, Tenn.) and results were expressed in the number of colony forming units (CFU) per gram of soil. The results are summarized in Table 2.

TABLE 2

Activity of Carbohydrate-based Surfactant Compositions on Soil Microbes

| Treatment (as described in text) | Microbe type | Pretreatment microbe count (CFU) | 60 Days post treatment microbe count (CFU) |
|---|---|---|---|
| No treatment | Bacteria | 10,000 | 475,000 |
| No treatment | Mold | 48,000 | 55,000 |
| No treatment | Yeast | 1 | 1 |
| SAFE-T GREEN | Bacteria | 10,000 | 1,040,000 |
| SAFE-T GREEN | Mold | 50,000 | 45,000 |
| SAFE-T GREEN | Yeast | 1 | 1 |
| AGRIMUL PG 2069 | Bacteria | 10,000 | 2,135,000 |
| AGRIMUL PG 2069 | Mold | 50,000 | 85,000 |
| AGRIMUL PG 2069 | Yeast | 1 | 10,000 |

The data summarized in Table 2 clearly show that agricultural compositions comprising AGRIMUL PG 2069 significantly improve the soil microbe populations. While the microbe populations did increase in the control plots these increases were small when compared with the proliferation measured in the AGRIMUL PG 2069 treated plots. Furthermore the AGRIMUL PG 2069 promoted microbial growth to 2 times the levels seen for the SAFE-T GREEN treated plots.

As the data indicates, the composition prepared using the AGRIMUL PG 2069 surfactant dramatically induced the proliferation of soil microbes. This increase was much larger than that seen for either the untreated samples or the samples treated with SAFE-T GREEN.

Example 5

Testing the Bioremediation Promoting Properties of AGRIMUL PG 2069 and Agricultural Compositions Thereof The composition of Example 2 was tested for enhanced biodegradation of trifluralin. Test sites of 100 square feet were used with each test replicated three times. The AGRIMUL PG 2069 was applied either as a liquid or mixed with fertilizer. When applied as a liquid the AGRIMUL PG 2069 was delivered at the rate of 1 quart/acre. The AGRIMUL PG 2069 was applied with water as a carrier. The amount of carrier was 40 gallons/acre. When applied with fertilizer the rate was 250 lb./acre. Soil samples were taken at 14 day intervals. 3 replicate samples were taken from the top six inches of soil in each plot. The samples were mixed and a single sample of this mixture was used as a representative sample. The samples were tested for trifluralin. The results are shown in Table 3.

TABLE 3

Enhanced Bioremediation of Herbicide Contaminated Soil using Carbohydrate-based Surfactants.

| Treatment | Test Site | Initial concentration of Trifluralin (ppm) | Trifluralin (ppm) 14 days post treatment | Trifluralin (ppm) 28 days post treatment; | Trifluralin (ppm) 42 days post treatment |
|---|---|---|---|---|---|
| 1 | 2 | 10 | 10 | 10 | 9 |
| 2 | 2 | 10 | 8 | 7 | 7 |
| 3 | 2 | 10 | 5 | 3 | 1 |

Treatments:
1. trifluralin
2. trifluralin + AGRIMUL PG 2069
3. trifluralin + AGRIMUL PG 2069/fertilizer mixture

Example 6

Tomato Field Study

This study was conducted to find if a carbohydrate surfactant applied to fertilizer would promote plant growth above fertilizer alone. The study evaluates the influence of Agrimul PG 2069 carbohydrate surfactant coated onto fertilizer as described in Example 2. Tomato foliage, fruit numbers and weight, root gall severity, and final harvest soil population density of *Meloidogyne incognita* on susceptible (FL 47) tomato cultivar during fall 1999, in field microplots at CREC, Lake Alfred, Fla. were evaluated.

TABLE 4

Tomato Field Study.

| Treatment | Rate | Foliage Wt. | Total Fruits No. | Total Fruit Wt. | Root Gall |
|---|---|---|---|---|---|
| 1. Fertilizer | 250 #/A | 1027.9 g | 19.3 | 1243.6 g | 7.4 |
| 2. PG 2069 + Fert. | 1 qt./A 250#/A | 1087.0 g | 23.0 | 1690.3 g | 7.3 |

The carbohydrate surfactant+fertilizer had little effect on foliage weight. The plant maintained normal growth patterns even with high nematode populations. The plant food went to fruit production and not foliage as seen in the 19% increase in total fruit numbers. The carbohydrate surfactant (Agrimul PG-2069)+fertilizer gave a 36% increase in fruit weight over fertilize alone. This shows that the treated plots had larger tomatoes that give a better grade price. There was no difference in root gall caused by nematodes. The population density of incognita was not taken.

Example 7

Carrot Field Study

This study was conducted to find if a carbohydrate surfactant applied to fertilizer would promote plant growth above fertilizer alone. The study evaluates the influence of Agrimul PG 2069, carbohydrate surfactant, coated onto fertilizer against fertilizer alone. Test data collected was for marketable pounds per acre, total number of carrots with nematode damage, total pounds per acre nematodes effected, and total number of marketable carrots. This research was conducted at the University of Georgia at Tifton, Ga. in the spring of 2000. Agrimul PG 2069 was applied at a rate of 1 qt. per acre coated onto the fertilizer as described in Example 2.

TABLE 5

Carrot Field Study.

| Treatment | Lbs./Acre | No./Acre | No. of nematode damaged | Lbs. effected by nematodes |
|---|---|---|---|---|
| Agrimul PG 2069 + 10-10-10 | 25,846 | 105,633 | 62,799 | 8,222 |
| 10-10-10 | 18,440 | 78,045 | 85,305 | 13,431 |

Agrimul PG 2069 (carbohydrate surfactant) coated onto 10-10-10 fertilizer promoted better plant growth than did 10-10-10 fertilizer alone. The Agrimul PG 2069 plots had 40% greater yield in total pounds, 35% greater number of carrots per acre, 35% less nematode damaged, and 63% more pounds of healthy carrots.

Example 8

Potato Field Study

This study was conducted to find if a carbohydrate surfactant ,Agrimul PG 2069, applied to fertilizer would promote plant growth above fertilizer alone. The study evaluates the influence of Agrimul PG 2069 carbohydrate surfactant coated onto fertilizer against fertilizer alone. The crop tested was red potatoes. The test site was in south Florida and conducted by the crop owners. This test was conducted for the year 2000 crop. Agrimul PG 2069 was applied onto the fertilizer at a rate of 1 qt./acre. Agrimul PG 2069 was sprayed into the fertilizer mixer and allowed to thoroughly mix, as described in Example2.

Agrimul PG 2069 (1 qt./acre)+fertilizer yielded 400 bags per acre.

Fertilizer alone yielded 310 bags per acre.

The Agrimul PG 2069 treated acres gave a 29% increase of harvested potatoes.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods in the steps or in the sequence of steps of the methods described herein without departing from the concept, spirit and scope of the invention. It will also be apparent that certain agents which are both chemically and physiologically related may be substituted for the agents described herein to achieve the same or similar results. All such similar substitutes and modifications apparent to those skilled in the art are deemed to be within the spirit, scope and concept of the invention.

What is claimed is:

1. An agricultural composition consisting of a carbohydrate-based surfactant coated on the surface of a solid soil additive fertilizer; and optionally a drying agent; wherein the carbohydrate-based surfactant is selected from the group consisting of alkyl polyglycosides, alkyl glucosides, fatty acid glucamides, sucrose fatty acid esters, and sorbitan fatty acid esters; and wherein the composition consists of 400 grams to 7700 grams of surfactant for each U.S. ton of solid soil additive fertilizer.

2. The agricultural composition of claim 1, wherein the soil additive fertilizer is a powdered, particulate, granular, or pelleted form.

3. The agricultural composition of claim 1, wherein the fertilizer is ammonium nitrate, ammonium sulfate, ammonium polyphosphate, calcium nitrate, calcium sulfate, diammonium phosphate, triple super phosphate, single super phosphate, lime or limestone, magnesium sulfate, manganese sulfate, monoammonium phosphate, monocalcium phosphate, potassium nitrate, potassium chloride, potassium magnesium sulfate, sulfate of potash, sodium nitrate, sulfur-coated urea, borax, pelleted fertilizers, fertilizers coated for slow release, or mixtures thereof.

4. The agricultural composition of claim 1, wherein the drying agent is diatomaceous earth, calcium sulfate, corn cob particulate, bentonite clay, vermiculite, or combinations thereof.

5. The agricultural composition of claim 1, wherein the surfactant is represented by the formula:

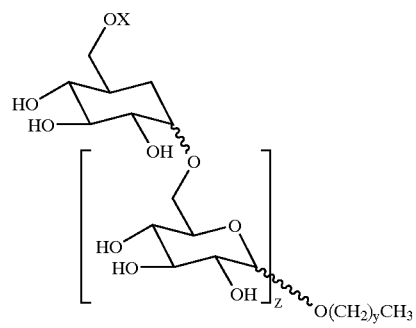

wherein (y) is an integer from 7 to 21; (z) is any number between 1 and 10; and (x) is defined as a carbonate group, ethercarboxylate group, ether group, ethoxylate group, ester group, hydrogen atom, isethionate group, quaternary group, sulfate group, or sulfosuccinate group.

6. The agricultural composition of claim 1, wherein (y) is 7 to 14, (z) is 1.0 to 1.8, and (x) is an hydrogen atom.

7. The agricultural composition of claim 1, wherein between about 400 grams and about 2900 grams of the surfactant are applied to each U.S. ton of solid soil additive.

* * * * *

UNITED STATES PATENT AND TRADEMARK OFFICE
CERTIFICATE OF CORRECTION

PATENT NO. : 6,565,860 B1
DATED : May 20, 2003
INVENTOR(S) : Richard T. Walker

It is certified that error appears in the above-identified patent and that said Letters Patent is hereby corrected as shown below:

<u>Column 14,</u>
Lines 16-30, replace the structure as shown below:

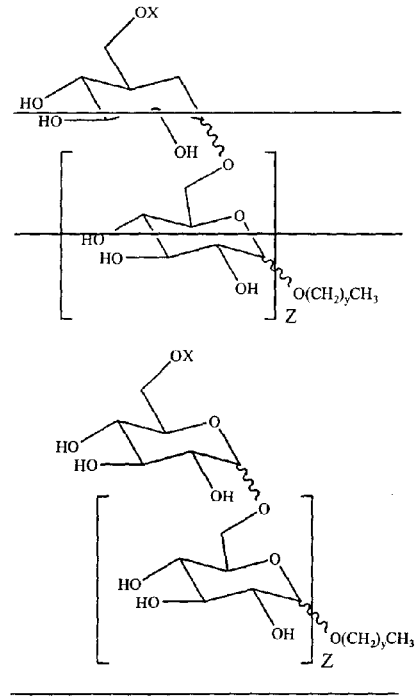

Signed and Sealed this

Twentieth Day of January, 2004

JON W. DUDAS
*Acting Director of the United States Patent and Trademark Office*